United States Patent [19]

Tachibana et al.

[11] Patent Number: 5,011,765
[45] Date of Patent: Apr. 30, 1991

[54] DYE FORMING COUPLER FOR PHOTOGRAPHIC USE

[75] Inventors: Kimie Tachibana, Hino; Yutaka Kaneko, Sagamihara, both of Japan

[73] Assignee: Konica Corporation, Tokyo, Japan

[21] Appl. No.: 541,463

[22] Filed: Jun. 22, 1990

Related U.S. Application Data

[62] Division of Ser. No. 284,522, Dec. 15, 1988, abandoned.

[30] Foreign Application Priority Data

Feb. 15, 1988 [JP] Japan .................. 63-32094

[51] Int. Cl.$^5$ .............................. G03C 7/38
[52] U.S. Cl. .................... 430/548; 430/558; 544/229; 544/244; 544/250
[58] Field of Search ............ 430/548, 558 R; 544/229, 244, 250

[56] References Cited

U.S. PATENT DOCUMENTS

| | | | |
|---|---|---|---|
| 3,150,136 | 9/1964 | Wolfram et al. | 544/250 |
| 3,171,740 | 3/1965 | Menzel et al. | 430/558 |
| 4,198,235 | 4/1980 | Vetter et al. | 430/223 |
| 4,461,827 | 7/1984 | Bergthaller et al. | 430/223 |
| 4,473,632 | 9/1984 | Kitaguchi et al. | 430/223 |
| 4,713,321 | 12/1987 | Mifune et al. | 430/569 |
| 4,950,585 | 8/1990 | Tachibana et al. | 430/558 |

OTHER PUBLICATIONS

Hahn et al., *Chem. Abstr.* No. 123427x, vol. 103, 1985.
Chemical Abstracts-11 Coll. Index, pp. 58234CS-58235CS.

*Primary Examiner*—Richard L. Schilling
*Attorney, Agent, or Firm*—Finnegan, Henderson, Farabow, Garrett, and Dunner

[57] ABSTRACT

A novel cyan dye-forming coupler suitable for color photographic materials is disclosed. The coupler forms a cyan dye images excellent in resistivities to heat and moisture and fastness to light. The coupler has the following a chemical structure of Formula I;

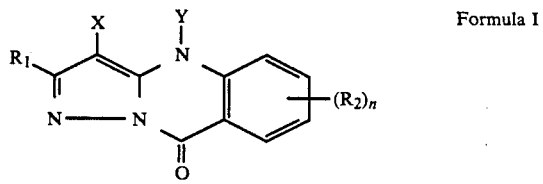

Formula I wherein X represents a group a group or atom, except hydrogen atom, capable of being split off upon reaction with the oxidized product of a color developing agent; $R_1$, $R_2$ and Y individually represent a hydrogen atom or a substituent; n is an integer of zero to 4, provided that the $R_2$s may be the same with or different from each other when n is 2, 3 or 4.

4 Claims, No Drawings

DYE FORMING COUPLER FOR PHOTOGRAPHIC USE

This application is a division, of U.S. application Ser. No. 07/284,522, filed Dec. 15, 1988 now abandoned.

FIELD OF THE INVENTION

The present invention relates to the novel couplers for color photography and, more particularly, to ones for producing dye images which are excellent specifically in resistances to heat and moisture and fastness to light.

BACKGROUND OF THE INVENTION

A silver halide photographic light-sensitive material after image wise exposure forms the image in color by a color developing process wherein, in the exposed area, the oxidized product of an aromatic primary amine color developing agent reacts with a dye-forming coupler to produce a dye.

Generally in this photographic method, images in yellow, magenta and cyan are formed for reproducing the color images by substractive color reproduction method.

As couplers for producing images in color in the above-mentioned method, there are, for example, ones of the acylacetanilide type for yellow, ones of the types of pyrazolone, pyrazolobenzimidazol, pyrazolotriazol, and indazolone for magenta, and ones of the phenol and the naphthol types for cyan.

It is desired that the dye images obtained by the above-mentioned method do not discolor or fade when they are exposed to light for a long time or kept under high temperature or highly humid condition.

However, the fact is that the phenol-type and the naphthol-type couplers, on which the past studies for cyan dyes have centered, do not quite measure up to the expectations in respect of the spectral absorption characteristics, resistances to heat moisture, and the like of the cyan dye images produced.

On the other hand, for magenta, the use of 5-pyrazolone-based couplers, on which the studies have centered and which have been in wide use, are satisfactory in respect of the fastness of the dye images against heat and light, but the dye produced is lacking in pureness with an unwanted absorption of yellow as a component. To solve this problem, there have been proposals to use couplers of the types of pyrazolobenzimidazol, indazolone, pyrazolotriazol, imidazopyrazol, pyrazolopyrazol, pyrazolotetrazol, etc. Indeed the dyes produced by using these couplers are satisfactory in point of reproduction of color, but at the sacrifice of the fastness to light, which so retrogrades as to cause discoloration or fading.

In this connection U.S. Pat. No. 3,171,740 describes couplers consisting of compounds of the type of pyrazolo [1',5':3,2]-quinazolone, which indeed are satisfactory in respect of the spectral absorption characteristics, and the resistances to heat, moisture and light of the dye images produced. However, all of these couplers are of four equivalents, so that the development requires a relatively large quantity of silver halide, that is to say, to produce 1 mole of dye by reacting with the oxidized product of an aromatic primary amine color developing agent such a coupler theoretically requires 4 moles of silver halide to be developed.

As contrasted, a coupler of two equivalents requires only 2 moles of silver halide to be developed.

Furthermore, it has been found that photographic light-sensitive materials prepared by using the couplers in the description of the above-mentioned U.S. patent retrograde in photographic performance when made to stand in a hot, highly humid environment, this defect involving degradation of the sensitivity.

The research undertaken by the present inventors with the objective of solving the aforementioned problems has resulted in new two-equivalent couplers for forming photographic light-sensitive materials which are excellent in stability in storage and the dye images produced thereby are resistant to heat, moisture and light with respect to their influences on the hue.

SUMMARY OF THE INVENTION

A first object of the present invention is to provide new two-equivalent couplers as materials for color photography.

A second object of the present invention is to provide two-equivalent couplers for producing dye images whose hue is stable to heat, moisture and light.

A third object of the present invention is to provide two-equivalent couplers as materials for color photographic light-sensitive materials, which render the photographic materials secure from degradation of the photographic performance, especially with respect to the sensitivity, during storage.

The above-mentioned objects of the present invention have been accomplished by a cyan dye-forming coupler represented by the following Formula I:

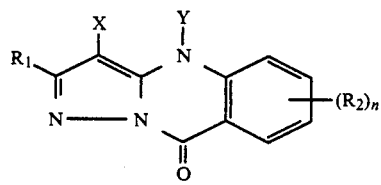

Formula I wherein X represents an atom, except hydrogen atom, or a group capable of being split off upon reaction with the oxidized product of a color developing agent; $R_1$ and $R_2$ and Y individually represent a hydrogen atom or a substituent; n is an integer of 0 to 4 provided that the $R_2$ may be the same with or different from each other when n is 2, 3 or 4.

DETAILED DESCRIPTION OF THE INVENTION

In the above-mentioned general formula I, X is a group bonded to an active site and can be split off by reaction with an oxidized product of a color developing agent, examples of this group being halogen atoms (chlorine atom, bromine atom, fluorine atom, etc.), groups of alkoxy, aryloxy, heterocyclic oxy, acyloxy, sulfonyloxy, alkoxycarbonyloxy, aryloxycarbonyloxy, alkyloxalyloxy, alkoxyoxalyloxy, alkylthio, arylthio, heterocyclic thio, alkyloxythiocarbonylthio, acylamino, sulfonamido, nitrogen-containing heterocycle bonded on N atoms, alkyloxycarbonylamino, aryloxycarbonylamino, and carboxyl, and group represented as

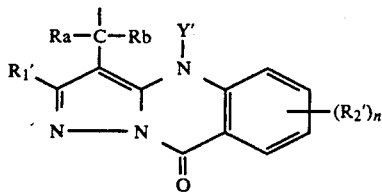

wherein $R_1'$, $R_2'$ and $Y'$ have the same signification as the aforementioned $R_1$, $R_2$ and $Y$, and $R_a$ and $R_b$ individually represent a hydrogen atom, an aryl group, an alkyl group, or a heterocyclic group, preferably halogen atoms, and most preferably a chlorine atom X does not include a hydrogen atom.

There are no specific restrictions to the use of substituents for $R_1$ and $R_2$ in the formula I, but typically useful are, for example, groups of alkyl, aryl, anilino, acylamino, sulfonamido, alkylthio, arylthio, alkenyl, and cycloalkyl. Also useful for the same purpose are halogen atoms and groups of, for example, cycloalkenyl, alkinyl, heterocycle, sulfonyl, sulfinyl, phosphonyl, acyl, carbamoyl, sulfamoyl, cyano, alkoxy, sulfonyloxy, aryloxy, heterocyclic-oxy, siloxy, acyloxy, carbamoyloxy, amino, alkylamino, imido, ureido, sulfamoylamino, alkoxycarbonylamino, aryloxycarbonylamino, alkoxycarbonyl, aryloxycarbonyl, heterocyclic-thio, thioureido, carboxy, hydroxy, mercapto, nitro, and sulfo as well as a spiro-compound residue, a bridged hydrocarbon compound residue, and the like.

The alkyl group taking the place of $R_1$ and $R_2$ may preferably be one of carbon number of 1 to 32 and may be of the straight-chain type as well as the branched-chain type.

Likewise, specific examples of the groups useful for $R_1$ and $R_2$ are as follows:

The aryl group may preferably be one of phenyl;

The acylamino group may be one of alkylcarbonylamino, one of arylcarbonylamino, or the like;

The sulfonamido group may be one of alkylsulfonylamino, one of arylsulfonylamino, or the like:

The alkyl component or the aryl component of the alkylthio group and the arylthio group may be an alkyl group or an aryl group represented by $R_1$ and $R_2$ as mentioned above;

The alkenyl group may be one of carbon number of 2 to 32 and can be of the straight-chain type as well as the branched-chain type, and the cycloalkyl group may be one of carbon number of 3 to 12 or especially preferably one of carbon number of 5 to 7;

The cycloalkenyl group may be one of carbon number of 3 to 12 or especially preferably one of carbon number of 5 to 7;

The sulfonyl group may be one of alkylsulfonyl, one of arylsulfonyl, or the like;

The sulfinyl group may be one of alkylsulfinyl, one of arylsulfinyl, or the like;

The phosphonyl group may be one of alkylphosphonyl, one of alkoxyphosphonyl, one of aryloxyphosphonyl, one of arylphosphonyl, or the like;

The acyl group may be one of alkylcarbonyl, one of arylcarbonyl, or the like;

The carbamoyl group may be one of alkylcarbamoyl, one of arylcarbamoyl, or the like;

The sulfamoyl group may be one of alkylsulfamoyl, one of arylsulfamoyl, or the like;

The acyloxy group may be one of alkylcarbonyloxy, one of arylcarbonyloxy, or the like;

The carbamoyloxy group may be one of alkylcarbamoyloxy, one of arylcarbamoyloxy, or the like;

The ureido group may be one of alkylureido, one of arylureido, or the like;

The sulfamoylamino group may be one of alkylsulfamoylamino, one of arylsulfamoylamino, or the like;

The heterocyclic group may preferably be one of 5 to 7 members, namely, one of 2-furyl, one of 2-thienyl, one of 2-phrimidinyl, one of 2-benzothiazolyl, one of 1-pyrrolyl, one of 1-tetrazolyl, or the like;

The heterocyclic-oxy group may preferably be one containing a heterocyclic ring of 5 to 7 members, namely, one of 3,4,5,6-tetrahydropyranyl-2-oxy, one of 1-phenyltetrazol-5-oxy, or the like;

The heterocyclic-thio group may preferably be one of 5 to 7 members, namely, one of 2-pyridylthio, one of 2-benzothiazolylthio, one of 2,4-diphenoxy-1,3,5-triazol-6-thio, or the like;

The siloxy group may be one of trimethylsiloxy, one of triethylsiloxy, one of dimethylbutylsiloxy, or the like;

The imido group may be one of succinimido, one of 3-heptadecylsuccinimido, one of phthalimido, one of glutarimido, or the like;

The spiro-compound residue may be one of spiro[3,3-]heptane-1-yl, or the like;

The bridged hydrocarbon compound residue may be one of bicyclo[2,2,1]heptane-1-yl, one of tricyclo[3,3,1,1$^{37}$]decane-1-yl, one of 7,7-dimethyl-bicyclo[2,2,1]heptane-1-yl, or the like. Any of these groups, furthermore, may contain a substituent such as a non-diffusible group which may be a long chain hydrocarbon group, a polymer residue, or the like.

Y in the formula I represents a hydrogen atom or a substituent, this substituent preferably being one which, for example, after the compound embodying the present invention has reacted with the oxidized product of the developing agent, splits off from said compound. Examples of the substituent represented by Y are one, such as benzoyl group, which releases under alkaline condition as described in Japanese Patent Publication Open to Public Inspection No. 61-228444/1986 and one, such as a coupler residual represented by

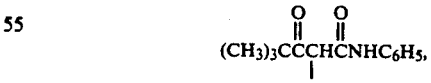

which comes off by coupling reaction with the oxidation product of the developing agent takes place as described in Japanese Patent Publication Open to Public Inspection No. 56-133734/1981. Nevertheless, it is preferable for Y to have a hydrogen atom.

Some typical examples of the compounds represented by the formula I are shown next on the understanding that these examples shall by no means restrict the scope of the present invention.

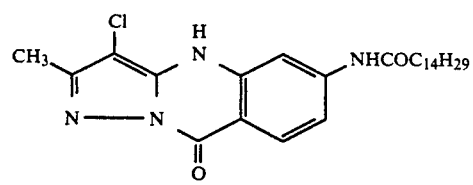 (1)
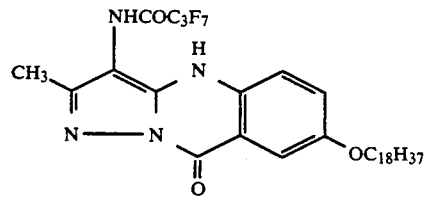 (2)
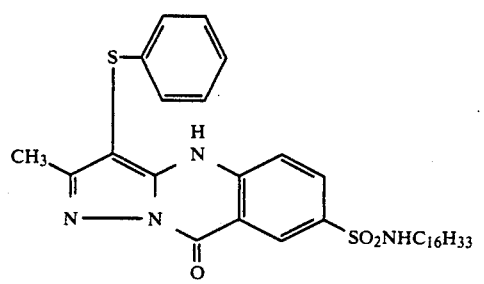 (3)
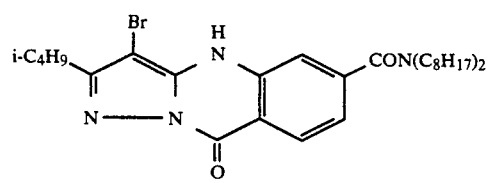 (4)
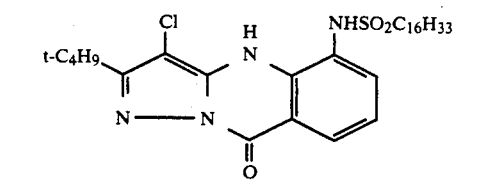 (5)
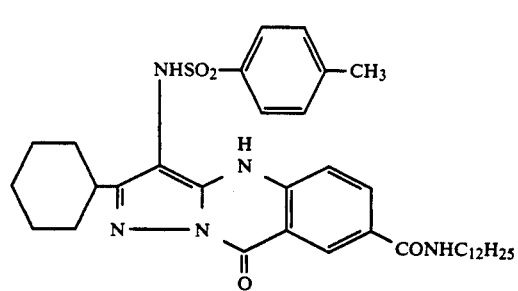 (6)
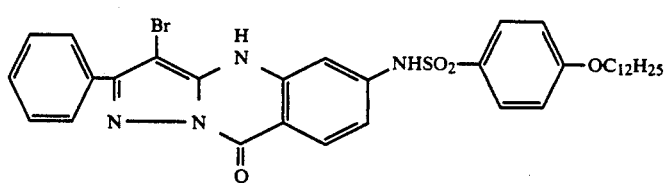 (7)
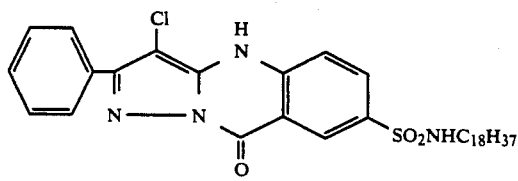 (8)

-continued
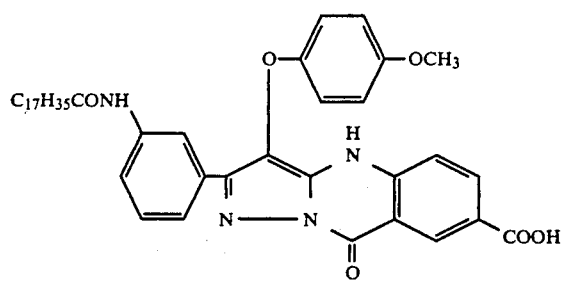
(9)
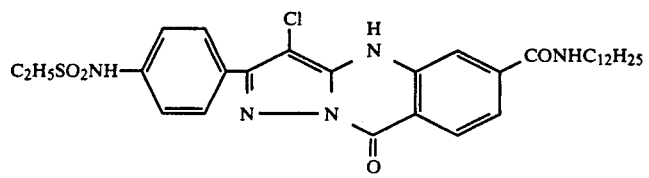
(10)
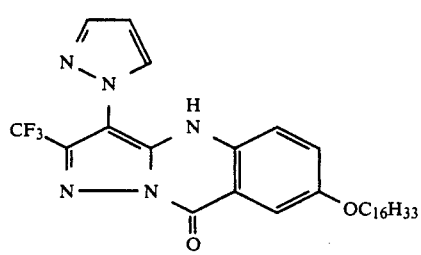
(11)
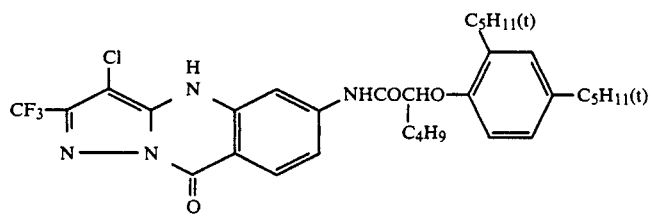
(12)
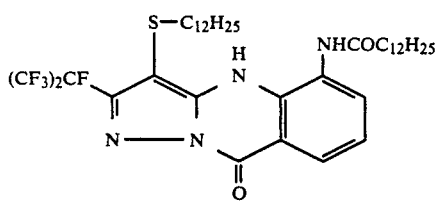
(13)
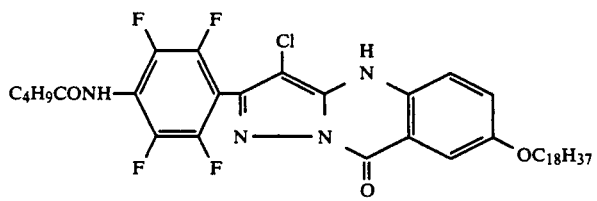
(14)
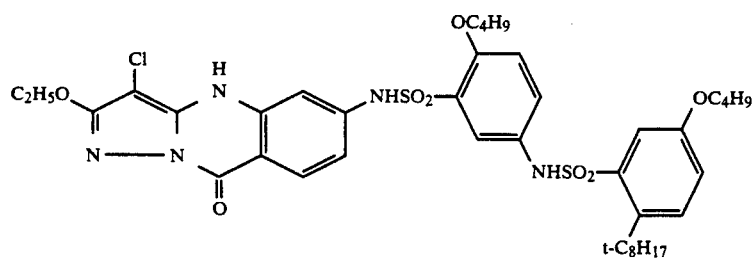
(15)

-continued
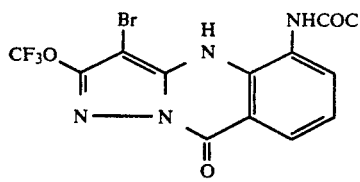
(16)
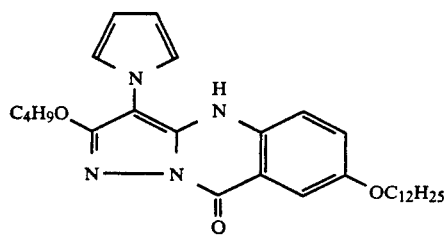
(17)
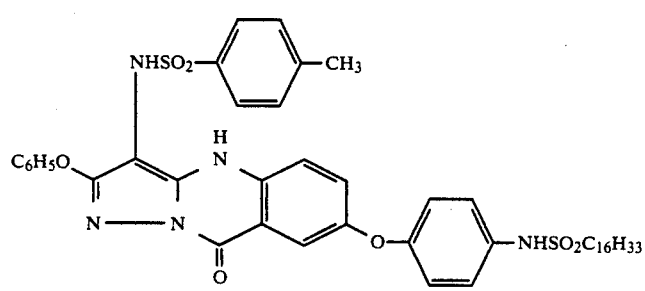
(18)
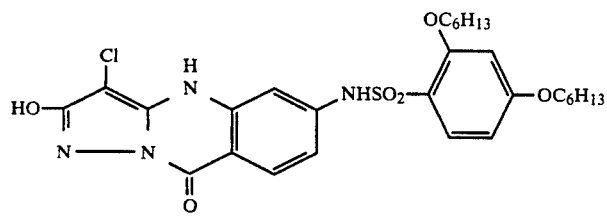
(19)
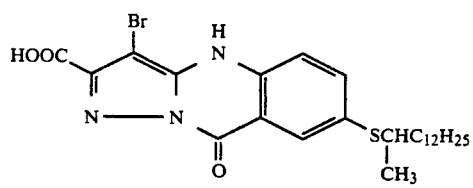
(20)
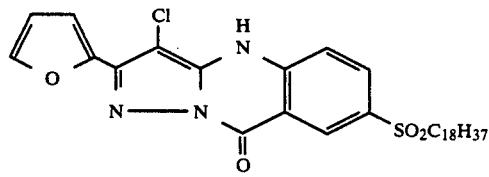
(21)
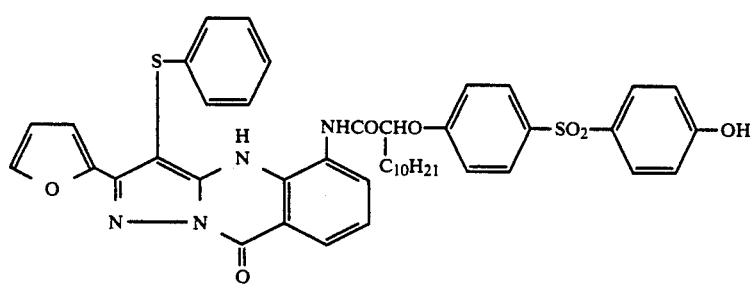
(22)

-continued
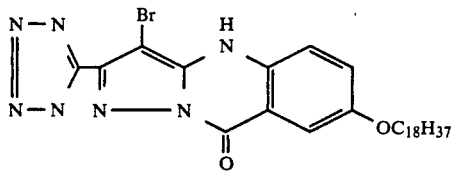
(23)
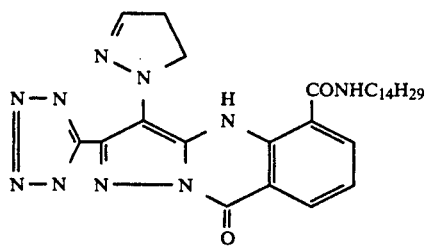
(24)
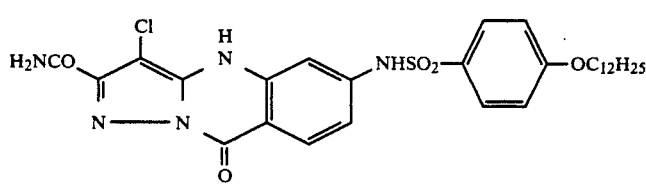
(25)
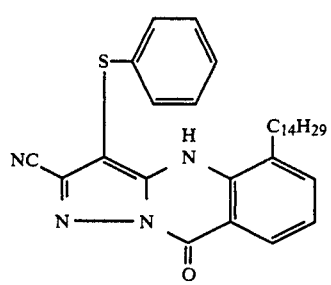
(26)
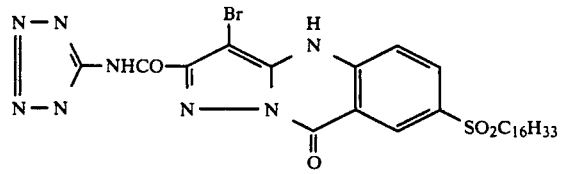
(27)
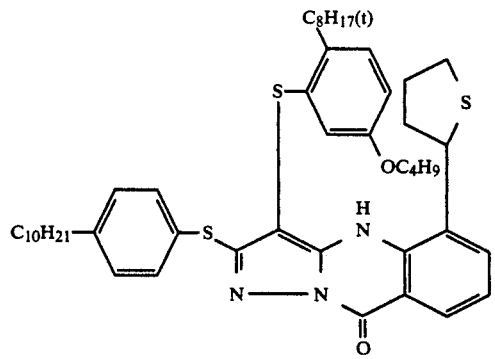
(28)
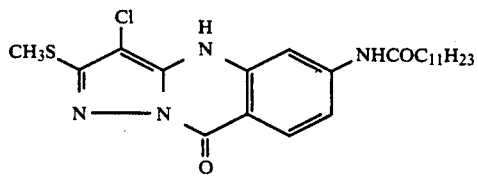
(29)

-continued
(30)
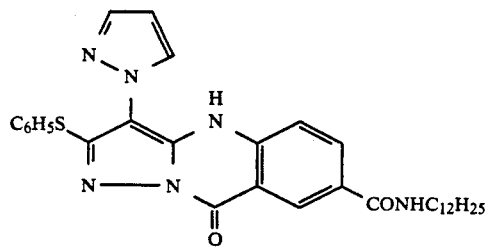
(31)
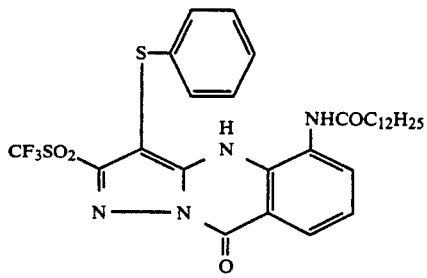
(32)
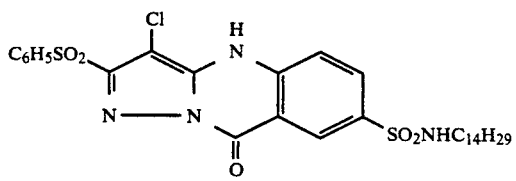
(33)
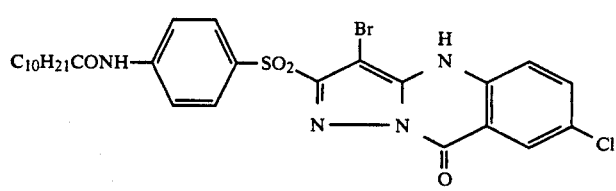
(34)
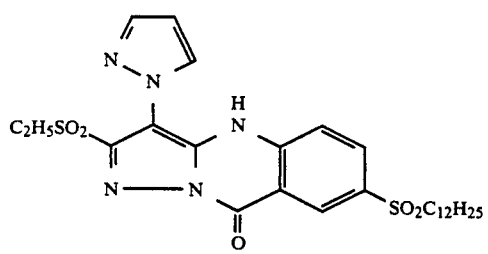
(35)
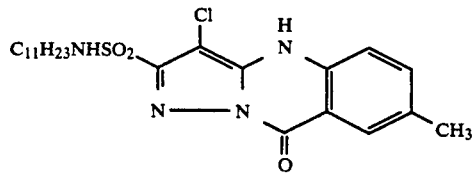
(36)
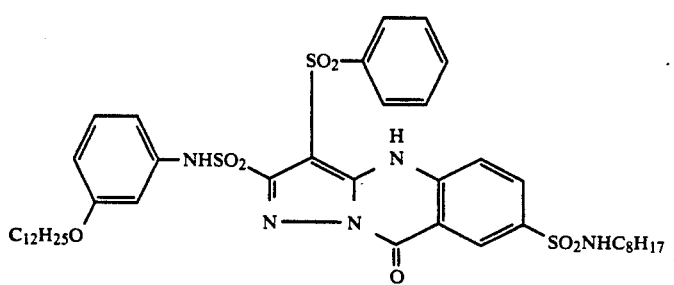

-continued
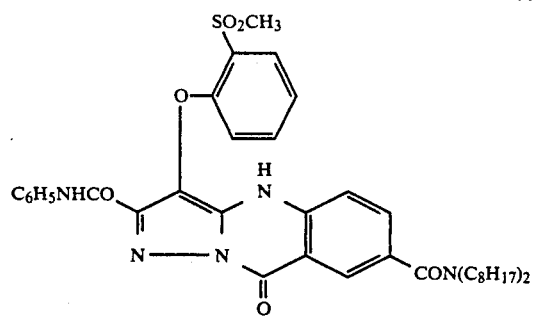
(37)
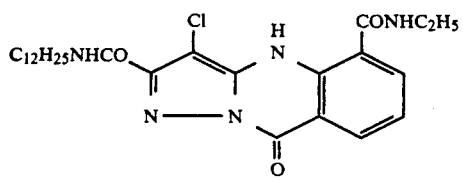
(38)
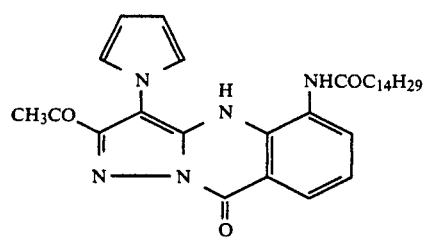
(39)
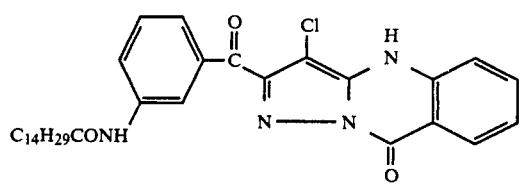
(40)
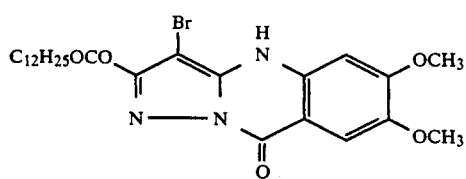
(41)
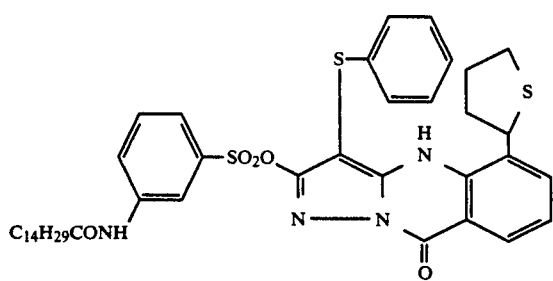
(42)
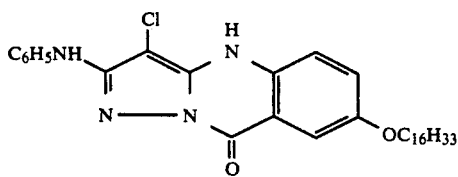
(43)

-continued

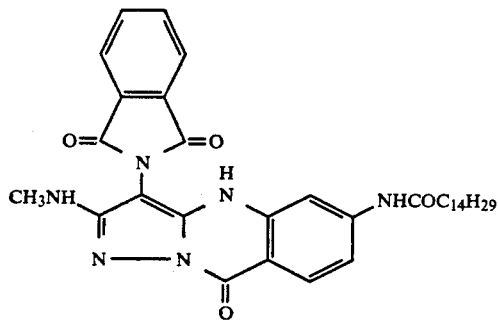
(44)

A photographic coupler embodying the present invention can be synthesized by a method wherein, as described by the examples of the synthesis below, to the active site of a pyrazolo-[1':5':3,2]-quinazolone-based compound, a group which can be split off by reaction with an oxidation product of a color developing agent is bonded, said pyrazolo-[1':5':3,2]-quinazolone-based compound having been synthesized referring to West German Patent No. 1,111,505, U.S. Pat. Nos. 4,261,996 and 4,247,555, and the like.

SYNTHESIS 1
(Synthesis of Compound (45))

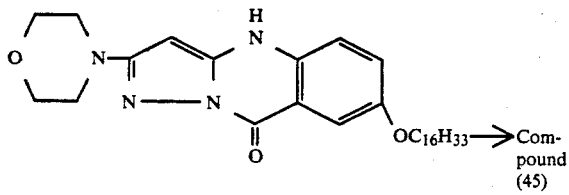

Twenty-five point five grams (0.05 mole) of a was dissolved in 500 ml of tetrahydrofuran and the solution obtained was cooled to a temperature below 5° C., and then 6.7 g (0.05 mole) of N-chlorosuccinimide was added little by little thereto. After this addition the tetrahydrofuran was distilled off under reduced pressure, and the residue was put in water so that the crystalline precipitate was filtered off. Through recrystallization of the precipitate with acetonitrile Compound (45) was obtained in the form of white needle crystals in a quantity of 18.5 g (yield 68%).

SYNTHESIS 2
(Synthesis of Compound (30))

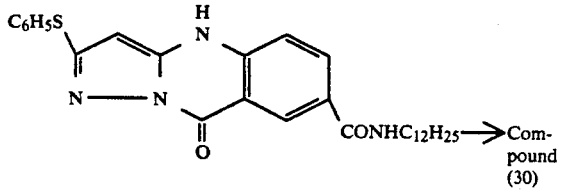

Twenty-five point two grams (0.05 mole) of b and 8.3 g (0.12 mole) of pyrazole were mixed with 30 ml of N,N-dimethylformamide and the mixture was stirred at 60° C. for 7 hours. After being allowed to cool at room temperature the mixture was put in 100 ml of water. The mixture was extracted with 100 ml of ethyl acetate and the solvent was concentrated under reduced pressure. Through recrystallization of the residue with acetonitrile Compound (30) was obtained in the form of white needle crystals in a quantity of 14.2 g (yield 50%).

A coupler of the present invention can be used normally in the range of $1 \times 10^{-3}$ mole$-1$ mole per 1 mole silver halide, or preferably in the range of $1 \times 10^{-2}$ mole$-8 \times 10^{-1}$ mole, and also in combination with a coupler of a different type.

The methods and techniques applicable to the use of ordinary dye-forming couplers are equally applicable to the use of the couplers of this invention.

The couplers of this invention as materials for color photography are applicable to all methods of color formation, specifically to all manner of coupler-in-developer processes as well as coupler-in-emulsion processes of color development.

In the case of a coupler-in developer process of color photograph development, a coupler of this invention is dissolved in an alkaline aqueous solution or an organic solvent (eg. an alcohol) when added to the developing solution.

In the case of a coupler-in-emulsion process of color photograph development, a coupler of this invention is used in a photographic light-sensitive material. Typically in this case, it is preferred for the coupler to be incorporated in a silver halide emulsion so that the photographic light-sensitive material can be formed by coating a support with the emulsion.

The couplers of this invention can be used for color photographic light-sensitive materials such as a color negative film as well as color positive films, cold printing paper, and the like, and are applicable to such photosensitive materials for multicolor photography as well as for mono color photography.

A coupler of this invention in the application to a photosensitive material for multicolor photography can be contained in any layer, but ordinarily it is to be contained in the red-sensitive silver halide emulsion layer.

A photosensitive material for multicolor photography has dye image-forming structural units which are photosensitive respectively to the three primary colors each in a certain spectral region. Each of said structural units may consists of a single of a plurality of emulsion layers which are photosensitive to a certain spectral region. The layers which compose a photosensitive material, including the dye image-forming structural units, can be mutually arranged in various ordinary orders known to the photographic manufacturers.

A typical photosensitive material for multicolor photography is composed of a cyan dye image-forming structural unit which comprises at the least one layer of red-sensitive silver halide emulsion containing at the least one cyan coupler, a magenta dye image-forming structural unit which consists at the least one layer of green-sensitive silver halide emulsion containing at least one magenta coupler and a yellow dye image-forming structural unit which comprises at least one layer of blue-sensitive silver halide emulsion containing at least one yellow coupler, all these structural units being laid on a support.

Such a photosensitive material may have more additional layers, such as a filter layer, an intermediate layer, a protective layer, and a subbing layer.

A conventional known method is applicable to the preparation of a photographic emulsion containing a cyan coupler of this invention. For example, a coupler of this invention singly or together with a different coupler is dissolved in an organic solvent which is either of the high boiling-point type with the boiling point above 175° C., such as tricresylphosphate or dibutyl phthalate, or of the low boiling-point type, such as butyl acetate or butyl propionate, or which may be a mixture of some of such solvents as occasion requires, and this solution, after being mixed with an aqueous gelatin solution containing a surface-active agent, is emulsified by a high speed mixer or a coloid mill. The resulting emulsion is added to a silver halide to finally form a silver halide emulsion embodying the present invention.

A coupler of this invention can be used advantageously in a photosensitive material whose silver halide component is a silver chloride, a silver chloro-bromide, or a silver chloro-iodo-bromide. The silver halide component can as well be a combination of such silver halides, such as a mixture of a silver chloride and a silver bromide. Where, for instance, a silver halide emulsion is used for color printing paper, the development performance is required to be especially speedy. In such cases it is preferable for the silver halide to contain chlorine atoms as a halide constituent, especially silver chloride, or a silver chloro-bromide or a silver chloroiodo-bromide containing at least 1% of silver chloride.

The silver halide emulsion can be chemically sensitized by a conventional method and also optically sensitized to a specified wavelength region as desired.

To the silver halide emulsion can be added compounds known to the photographic manufacturers as an antifogging agent and a stabilizer for the purpose of preventing fogging and/or stanbilizing the photographic performance during manufacture, storage or photographic processing of the photographic light-sensitive material.

To a color light-sensitive material wherein a coupler of this invention is used can be added an anti-color-fogging agent, dye-image stanbilizer, ultraviolet-proof agent, antistatic agent, matting agent, surface-active agent, and the like, which are ordinarily used in light-sensitive materials. A reference relevant to this can be found in Research Disclosure Vol. 176, pages 22-31 (December 1978).

For the development of the color photographic image a light-sensitive photographic material wherein a coupler of this invention is used can be subjected to a color developing process known to the photographic manufacturers.

A color photographic light-sensitive material using a coupler of this invention may have in a hydrophilic colloidal layer a color developing agent itself or its precursor so that for the development the photosensitive material can be treated by an activating alkaline bath.

A color photographic light-sensitive material using a coupler of this invention, after the color development, is subjected to a bleaching and a fixing processes. The bleaching and the fixing processes can be carried out simultaneously.

Said fixing process is ordinarily followed by a water-washing process. The washing can be replaced by a stabilizing process. Also the washing and the stabilizing processes can be carried out in combination.

EXAMPLES

The present invention will hereunder be explained in detail with reference to examples on the understanding that these examples shall by no means restrict the scope of the present invention.

EXAMPLE 1

A red-sensitive color photosensitive material, identified as Sample 1, was prepared by coating a paper support having polyethylene film on both sides in a laminate firstly with the undermentioned first layer and secondly with the next-mentioned second layer.

The amount of the addition of the compound in the examples is represented per square meter unless otherwise specified (the amount of the silver halide is a converted value representing the equivalent-silver). the First Layer (Emulsion Layer):

A red-sensitive emulsion layer consisting of 1.2 g of gelatin, 0.30 g of red-sensitive silver chloro-bromide emulsion (silver chloride content 96 mole%), and $9.1 \times 10^{-4}$ mole of cyan coupler (a) dissolved in 1,35 g of dioctyl phosphate for comparison. The Second Layer (Protective Layer):

A protective layer containing 0.50 g of gelatin, to which was added sodium salt of 2,4-dichloro-6-hydroxy-s-triazine as a hardener in a quantity of 0.017 g per 1 g gelatin.

Sample 2 for comperision and Sample 3 through Sample 10 embodying the present invention were prepared exactly in the same manner as Sample 1, except that the couplers listed in Table 1 were respectively substituted for the comparison coupler (a) (in the same mole quantity as the coupler (a)).

Sample 1 through Sample 10 thus obtained were subjected to wedge exposure by an ordinary method and to development in accordance with the following procedure.

| Developing Procedure: | | | |
| --- | --- | --- | --- |
| Color developing | 38° C. | 3 min. | 30 sec. |
| Beaching-Fixing | 38° C. | 1 min. | 30 sec. |
| Stabilizing/Washing | 25–30° C. | 3 min. | |
| Drying | 70–80° C. | 2 min. | |

The compositions of the treating solutions employed at the respective treating steps were as follows.

| Color Developer: | |
| --- | --- |
| Benzyl alcohol | 15 ml |
| Ethylene glycol | 15 ml |
| Potassium sulfite | 2.0 g |
| Potassium bromide | 0.7 g |
| Sodium chloride | 0.2 g |
| Potassium carbonate | 30.0 g |
| Hydrosulfate of hydroxylamine | 3.0 g |
| Sodium tripolyphosphate (TPPS) | 2.5 g |
| Hydrosulfate of 3-methyl-4-amino-N-ethyl-N-($\beta$-methanesulfonamide ethyl) aniline | 5.5 g |
| Fluorescent whitening agent (4,4'-diaminostilbenedisulfonic acid derivative) | 1.0 g |

| Color Developer: | |
|---|---|
| Potassium hydroxide | 2.0 g |

The total quantity was made 1 l by adding water and pH was adjusted to 10.20.

| Bleach-Fixer: | |
|---|---|
| Ferric ammonium ethylenediamine-tetraacetate dihydrate | 60 g |
| Ethylenediaminetetraacetic acid | 3 g |
| Ammonium thiosulfate (70% solution) | 100 ml |
| Ammonium sulfite (40% solution) | 27.5 ml |

The pH was adjusted to 7.1 with potassium carbonate or glacial acetic acid and the total quantity was made 1 l by adding water.

| Stabilizer: | |
|---|---|
| 5-chloro-2-methyl-4-isothiazolin-3-one | 1.0 g |
| Ethylene glycol | 10.0 g |
| The solution was made 1l by adding water. | |

Sample 1 through Sample 10, which had been processed as above, were subjected to measurement of the densities by a densitometer (Model KD-7, a product of Konica Corp.) and then, after being made to stand in a high temperature, high moisture environment (60° C., 80% RH) for 14 days, were examined in respect of the resistances of the dye image to heat and moisture.

The heat and moisture resistances of the dye images are expressed in terms of residual density of the dye image measured in percentage after the above-mentioned exposure to high temperature and high moisture with the initial density of the dye image as 1.0.

Table 1 shows the results.

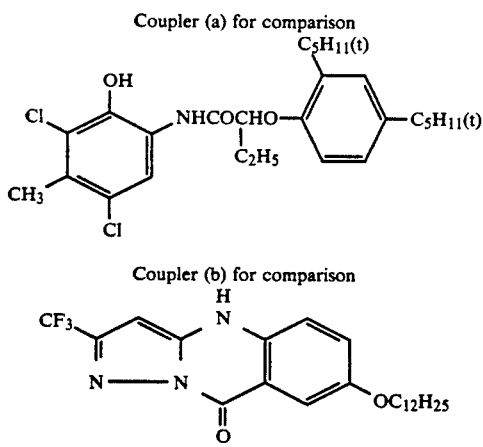

Coupler (a) for comparison

Coupler (b) for comparison

TABLE 1

| Sample No. | Coupler used | Dye-image residual rate (%) |
|---|---|---|
| 1 | Comparison coupler (a) | 62 |
| 2 | Comparison coupler (b) | 97 |
| 3 | Invention 8 | 95 |
| 4 | Invention 11 | 93 |
| 5 | Invention 21 | 96 |
| 6 | Invention 32 | 98 |
| 7 | Invention 34 | 97 |
| 8 | Invention 36 | 97 |
| 9 | Invention 38 | 95 |
| 10 | Invention 40 | 96 |

As is clear from Table 1, the samples using couplers of the present invention all showed high dye residual rates of cyan dye image, proving both the heat and moisture resistances to be excellent and indicating good fastness securing the dye images from changes in hue.

EXAMPLE 2

Four samples, Sample 11 through Sample 14, were prepared in the same manner as Sample 1 in Example 1, except that, instead of the red-sensitive silver chlorobromide emulsion (silver chloride content 96 mole %, 0.30 g) and the cyan coupler (a) for comparison, a green-sensitive silver chloro-bromide emulsion (silver bromide content 85 mole %) in a quantity of 0.35 g and the couplers of the present invention (1), (15), (18) and (43) each in a quantity of $5.1 \times 10^{-4}$ mole for the respective samples were used. These four samples were subjected to exposure and development in the same manner as in Example 1 and, after the treatment, they were examined in respect of their resistances to heat and moisture in the same manner as in Example 1.

The four samples were also tested in respect of light fastness by subjecting them to the irradiation in a xenon Fade-Ometer for 10 days and measuring the densities.

The resistances to heat and moisture as well as the light fastness of the dye image were tested in terms of residual density of the dye image measured in percentage after the above-mentioned respective testing steps with the initial density of the dye image as 1.0.

As a result, the samples using the couplers embodying the present invention each showed high dye residual rates of magenta dye image, proving all of the resistances to heat and moisuture and the light fastness to be excellent and indicating good fastness securing the dye images from changes in hue.

EXAMPLE 3

The same thirteen samples as Sample 2 through Sample 14 used in Example 1 and Example 2 were prepared anew each sample in a pair so that, while one odd series of the pairs were handled as fresh samples, the other halves of the pairs were made to stand in an environment having a temperature of 65° C. and a relative humidity of 80% for 2 days so as to have them undergo forced retrogradation.

The samples of both series were subjected to wedge exposure by an ordinary method and to the developing process in the same manner as in Example 1 and then each to color sensitometry to find the ratio of the sensitivity of each sample under forced degradation to that of the corresponding fresh sample as a relative sensitivity.

As a result, Sample 3 through Sample 14 using couplers embodying the present invention, as compared with Sample 2 using a coupler for comparison, were found little affected by said condition for forced retrogradation with their sensitivity virtually unimpaired and the photographic performance maintained satisfactory.

What is claimed is:

1. A silver halide photographic light-sensitive material comprising a support having thereon a silver halide emulsion layer containing a dye-forming coupler represented by Formula I:

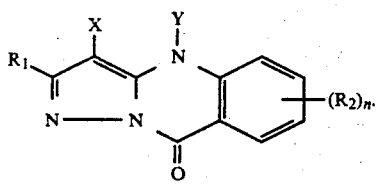

wherein $R_1$ and $R_2$ individually represent a hydrogen atom or a substituent selected from the group consisting of an alkyl group, an aryl group, an anilino group, an acylamino group, a sulfonamido group, an alkylthio group, an arylthio group, an alkenyl group, a cycloalky group, a halogen atom, a cycloalkenyl group, an alkinyl group, a heterocyclic group, a sulfonyl group, a sulfinyl group, a phosphonyl group, an acyl group, a carbamoyl group, a sulfamoyl group, a cyano group, an alkoxy group, a sulfonyloxy group, an aryloxy group, a heterocyclic-oxy group, a siloxy group, an acyloxy group, a carbamoyloxy group, an amino group, an alkylamino group, an imido group, a ureido group, a sulfamoylamino group, an alkoxycarbonylamino group, an aryloxycarbonylamino group, an alkoxtcarbonyl group, an aryloxycarbonyl group, a heterocyclic thio group, a thioureido group, a carboxyl group, a hydroxy group, a mercapto group, a nitro group, a sulfonic acid group, a spiro compound residue and a bridged hydrocarbon compound residue;

wherein Y is hydrogen or a group capable of splitting off after said coupler is coupled with the oxidized product of the color developing agent;

n is an integer of zero to 4, provided that the $R_2$s may be the same or different from each other when n is 2, 3 or 4;

X represents an atom or a group selected from the group consisting of a halogen atom, an alkoxy group, an aryloxy group, a heterocyclic-oxy group, an acyloxy group, a sulfonyloxy group, an alkylcarbonyloxy group, an aryloxycarbonyloxy group, an alkyloxalyloxy group, an alkoxyoxalyloxy group, an alkylthio group, an arylthio group, a heterocyclic-thio group, an alkyloxythiocarbonylthio group, an acylamino group, a nitrogen-containing heterocyclic group linked on a nitrogen atom, an alkyloxycarbonylamino group, a carboxyl group and a group represented by the formula:

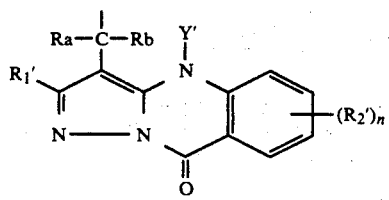

wherein $R_1'$, $R_2'$ and $Y'$ are selected from the same group from which said $R_1$, $R_2$ and Y are selected; and Ra and Rb individually represent a hydrogen atom, an aryl group, an alkyl group or a heterocyclic group, with the proviso that said atom or group represented by X is capable of being split off upon reaction with the oxidized product of a color developing agent.

2. The light-sensitive material of claim 1, wherein said X is a halogen atom.

3. The light-sensitive material of claim 2, wherein said X is a chlorine atom.

4. The light sensitive material of claim 1, wherein said Y is a hydrogen atom.

* * * * *

UNITED STATES PATENT AND TRADEMARK OFFICE
CERTIFICATE OF CORRECTION

PATENT NO. : 5,011,765
DATED : April 30, 1991
INVENTOR(S) : Kimie TACHIBANA et al.

It is certified that error appears in the above-identified patent and that said Letters Patent is hereby corrected as shown below:

Claim 1, Column 23, Line 30, change "alkoxt-" to
-- alkoxy- --.

Signed and Sealed this

Fifth Day of January, 1993

Attest:

DOUGLAS B. COMER

Attesting Officer

Acting Commissioner of Patents and Trademarks